US00PP16883P3

(12) United States Plant Patent
Whitcomb

(10) Patent No.: US PP16,883 P3
(45) Date of Patent: Jul. 25, 2006

(54) LACEBARK ELM TREE NAMED 'WHIT XXX'

(50) Latin Name: *Ulmus parvifolia*
Varietal Denomination: Whit XXX

(75) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 77 days.

(21) Appl. No.: 11/020,611

(22) Filed: Dec. 22, 2004

(65) Prior Publication Data

US 2006/0137052 P1 Jun. 22, 2006

(51) Int. Cl.
*A01H 5/00* (2006.01)

(52) U.S. Cl. ..... Plt./221
(58) Field of Classification Search ..... Plt./221
See application file for complete search history.

(56) References Cited

U.S. PATENT DOCUMENTS

| | | | | |
|---|---|---|---|---|
| PP5,554 P | 9/1985 | King | ..... | Plt./221 |
| PP6,983 P | 8/1989 | Karnosky | ..... | Plt./221 |
| PP7,240 P | 6/1990 | Rey | ..... | Plt./221 |
| PP7,551 P | 6/1991 | Glenn | ..... | Plt./221 |
| PP7,552 P | 6/1991 | Glenn | ..... | Plt./221 |
| PP10,732 P | 12/1998 | Wilkins | ..... | Plt./221 |
| PP10,846 P | 3/1999 | Cully | ..... | Plt./221 |
| PP11,295 P | 3/2000 | Moon | ..... | Plt./221 |

OTHER PUBLICATIONS

Patented Plants, Lacebark Inc. Horticulture Research [online], [retrieved on Sep. 19, 2005], Retrieved from the Internet <http://www.lacebarkinc.com/pat_plants.htm> pp. 1–3.*

Trademark Electronic Search System (TESS) [online], [retrieved on Sep. 19, 2005]. Retrieved from the Internet <http://tess2.uspto.gov/bin/showfield?f=doc&state=4332o 4.3.11> one page only.*

* cited by examiner

*Primary Examiner*—Kent Bell
*Assistant Examiner*—June Hwu
(74) *Attorney, Agent, or Firm*—Streets & Steele; Frank J. Campigotto; Jeffrey L. Streets

(57) ABSTRACT

A new and distinct lacebark elm tree, particularly distinguished in having an attractive upright-oval form, dark yellow-green leathery leaves and exceptional wood strength. The tree is easily propagated from cuttings to produce trees having a strong central leader and good stem taper without staking. The tree has proven resistant to common elm insects and diseases. The observed tree produces few seeds, none of which have been viable.

8 Drawing Sheets

Genus and species: *Ulmus parvifolia.*
Varietal denomination: Lacebark Elm 'Whit XXX'.

BACKGROUND OF THE INVENTION

Field of the Invention

This invention relates to a new and distinct variety or cultivar of the deciduous tree *Ulmus parvifolia,* commonly known as the lacebark elm.

Description of the Related Art

Lacebark elm, *Ulmus parvifolia,* was originally given the common name Chinese elm. Unfortunately, this common name was confusingly similar to the common name of *Ulmus pumil,* the Siberian elm. Because of the frequent confusion resulting from the similarity of these common names, Mr. E. W. Johnson of the U.S. Department of Agriculture and of Woodward, Okla. began referring to *Ulmus parvifolia* as lace-bark elm. Mr. Johnson used the common name lace-bark elm for *Ulmus parvifolia* in his writings on the introduction and study of trees for windbreaks: *Ornamental and Windbreak Trees for the Southern Great Plains,* USDA Crops Research Bulletin ARS 34–77 (1966). In 1973, the inventor of the present new cultivar began using and promoting the common name lacebark elm in his many writings as a substitute for the less suitable name Chinese elm. The name lacebark elm is now nearly universally accepted as the common name.

The lacebark elm is native to northern and central China, extending eastward into Korea. Typically, the lacebark elm is a large tree that matures to between about forty and about fifty feet tall and about the same dimensions wide. The lacebark elm is very adaptable to poor soil conditions and may be further characterized as having leaves that are dark green and having bark that is attractive.

The original seed from which this new cultivar is a descendent was collected south of Sian, China in 1914 and sent to the United States by U.S.D.A. plant explorer Frank N. Meyer. The resulting seedlings contributed to the Prairie State Forestry Project between 1935 and 1942 and the resulting 17,000 mile shelterbelt system. According to Mr. Johnson, at least a portion of the seed sent by Meyer ended up at the U.S.D.A. Southern Great Plains Field Station in Woodward, Okla. Mr. Johnson noted in 1966 that growth of *Ulmus parvifolia* seedlings was quite variable and that small leaved selections were typically more cold and drought tolerant.

The original seed used to develop this new cultivar was obtained by the inventor in 1972 from a large lacebark elm tree with small, glossy leaves located at the home of Mr. E. W. Johnson in Woodword, Okla. This large lacebark elm tree was grown from the seed sent back from Sian, China in 1914. The inventor also took cuttings from Mr. Johnson's tree on three occasions, but none rooted. However, thousands of lacebark elm seedlings were grown from those original seeds collected in 1972 from Mr. Johnson's tree.

By 1984, thirteen outstanding tree seedlings had been selected from all those grown from the seeds collected in 1972. However, each of these thirteen selections responded quite differently to attempts to propagate them from cuttings. No cuttings were ever rooted from 3 of the thirteen selections and these selections were discarded. Five selections rooted poorly, generally with a success rate of less than 25%, so these selections were also discarded. The five selections that rooted the best were studied in detail by Gary G. Hickman and the inventor. Of these five, only two grew moderately well following rooting of the cuttings, but the growth form of the offsprings from these two selections required considerable pruning and training at an early age to make desirable trees resembling the parents. These selections were judged to require excessive work to develop into desirable tree forms, so these selections were also discarded.

In 1984, the inventor wrote in his book entitled *Plant Production In Containers,* Lacebark Publications, Stillwater, Okla. (1984, 1988, 2003): "This study leaves little doubt about great differences among individual seedlings to root and grow into useful plants. If an outstanding tree is located, the first step is to determine if it will root from cuttings. The second step is to evaluate the growth and form and quality of the rooted cuttings. If the tree fails on either evaluation, look for other trees of the same species with good qualities and continue. Just because one tree of a species does not root or grow well does not mean that another specimen will respond the same way."

In 1988, seeds were collected from a desirable lacebark elm in Stillwater, Okla. that had resulted from the seeds collected in 1972 from the large lacebark elm tree of Mr. Johnson in Woodward, Olka. These seeds were planted, resulting in approximately sixty lacebark elm trees. The inventor then collected seeds from the two best specimens of these sixty lacebark elm trees and planted them in containers, resulting in approximately 2,000 tree seedlings. The most desirable of these seedlings, about 800, were selected and planted into the field for further evaluation. In the fall of 1996, seeds were collected by the inventor from two of these 800 trees, chosen for their demonstrated exceptional growth. The collected seeds from these two trees were planted, resulting in about 2800 seedlings. The inventor evaluated these seedlings, culling out the undersirable ones until only the best nine seedlings remained. These seedlings were characterized as having small leaves, exceptional vigor, a central leader and good form.

In February, 2002, when the nine selected trees were about 12 feet tall with a 3 inch stem diameter at the base, a severe ice storm occurred. Only one tree survived this ice storm with no damage and still standing upright, while the other eight trees were severely bent over and suffered broken limbs as a result of the ice. Then again in February, 2003 the nine trees were subjected to an even more severe ice storm and the same one tree, the new cultivar of the present invention, remained upright with no damage. One of the nine trees broke off near the ground as a result of the ice storm and the other seven trees were severely bent over and suffered broken limbs.

This new and distinct plant was asexually reproduced by rooting softwood cuttings taken from the original plant near Stillwater, Olka. The asexually reproduced plants show the unique features that characterize this new lacebark elm tree indicating that the unique features of this plant are stable through its successive generations of asexual reproduction. Furthermore, the asexually reproduced offspring grow with exceptional vigor and with a strong central leader stem unlike any before experienced by the inventor.

SUMMARY OF THE INVENTION

The present invention resulted from the discovery of a new and distinct variety of lacebark elm tree, *Ulmus parvifolia,* which has been given the cultivar name 'Whit XXX'. 'Whit XXX' is characterized as being a tree form with a central leader, exceptionally strong wood and developing an oval crown. Leaves are small, leathery and dark green.

As compared to other lacebark elm trees, the cultivar of the present invention has exceptionally strong wood. Generally, lacebark elm trees have been described as having limbs that are too flexible, e.g., bending down onto cars, the roofs of buildings and power lines. The lacebark elm has also been subject to breakage by ice or wet, heavy snow. The exceptionally strong wood of the present invention is demonstrated in FIG. 7, wherein the 'Whit XXX' cultivar is shown upright and undamaged following a severe ice event. Also shown, for comparison, is a severely ice-damaged tree of the same species, age and size.

As compared to other lacebark elm trees, the cultivar of the present invention is very resistant to *Cercospora* leaf spot disease. For example, two specimens of 'Allee' lacebark elm in three gallon containers, 6 specimens of 'UPMTF' (U.S. Plant Pat. No. 11,295 by Moon) and 6 specimens of 'Zettler' (U.S. Plant Pat. No. 10,846 by Cully) in one gallon containers were grown under the same irrigation and nursery conditions in north central Oklahoma. The 'Whit XXX' cultivar developed no *Cercospora* leaf spot while both the 'UPMTF' and 'Allee' cultivars were devoid of leaves, except at the very tips of branches, by early September due to *Cercospora.* The 'Zettler' cultivar developed moderate leaf spot, but the disease was clearly less severe compared to 'Allee' and 'UPMTF'. No fungicides were used during the testing for *Cercospora.* Furthermore, during the testing, no specific inoculations using the pathogen were made; rather, the pathogen was allowed to move as it naturally does in a nursery environment. Therefore, under the conditions of the evaluation, the 'Whit XXX' cultivar is less susceptible to *Cercospora* leaf spot when compared to 'Zettler' and much less susceptible to *Cercospora* leaf spot when compared to 'Allee' and 'UPMTF'.

The cultivar of the present invention may be further characterized as producing few viable seeds. Modest numbers of seed coats are produced in the fall of the year, but counts have shown that on average during both 2004 and 2005, there is only about one of what appears to be a developed seed out of about 15 seed coats. Further, in the fall of 2004, slightly more than 9 ounces of seeds/seed coats (no attempt was made to pick out the seed coats with what appeared to be a viable seeds from those without) were collected, stored over winter and planted in a greenhouse in the spring. From that planting, only 8 seedlings developed, which demonstrates very low viability of the seeds. Being nearly sterile is highly desirable in that it reduces the likelihood of seeds from the tree being dispersed by the wind and becoming weeds in the landscape. Other elms, such as Siberian elm and American elm, are landscape pests over much of the United States as their seeds blow in the wind, light in some small irregular space, germinate and establish themselves where they are not wanted.

BRIEF DESCRIPTIONS OF THE DRAWINGS

BOTANICAL DESCRIPTION OF THE PLANT

The following botanical description is of the new and distinct cultivar of lacebark elm tree, *Ulmus parvifolia,* named 'WHIT XXX'. Specific color designations set forth by number designations are in accordance with The Royal Horticultural Society Colour Chart. General color recitations are consistent with ordinary American color terminology.

The lacebark elm 'WHIT XXX' has not been observed under all possible environmental conditions. It is to be understood that the phenotype may vary significantly with variations in environment such as soils, temperature, light intensity and length of day without differences in the genotype of the plant. The following botanical characteristics and observations are taken from the plant when grown under normal outdoor conditions in north central Oklahoma. The described plant was about eight years old growing in a field in north central Oklahoma.

THE PLANT

Type: Deciduous woody tree with a single or multiple stems.

Classification: Lacebark Elm, *Ulmus parvifolia.*

Figure 1:
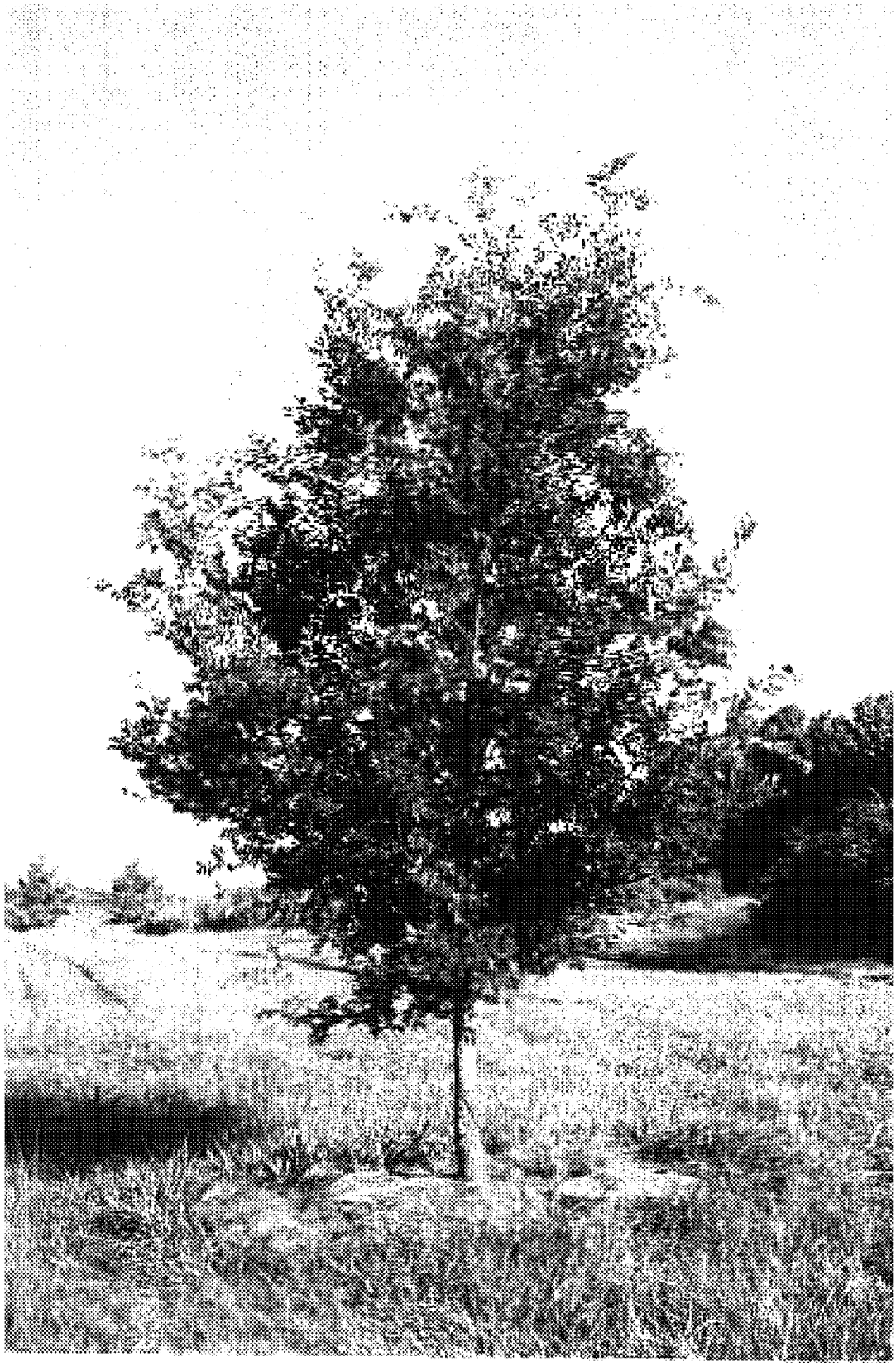
FIG. 1 is a full color photographic view of my new lacebark elm tree near Stillwater, Okla.
Figure 8:
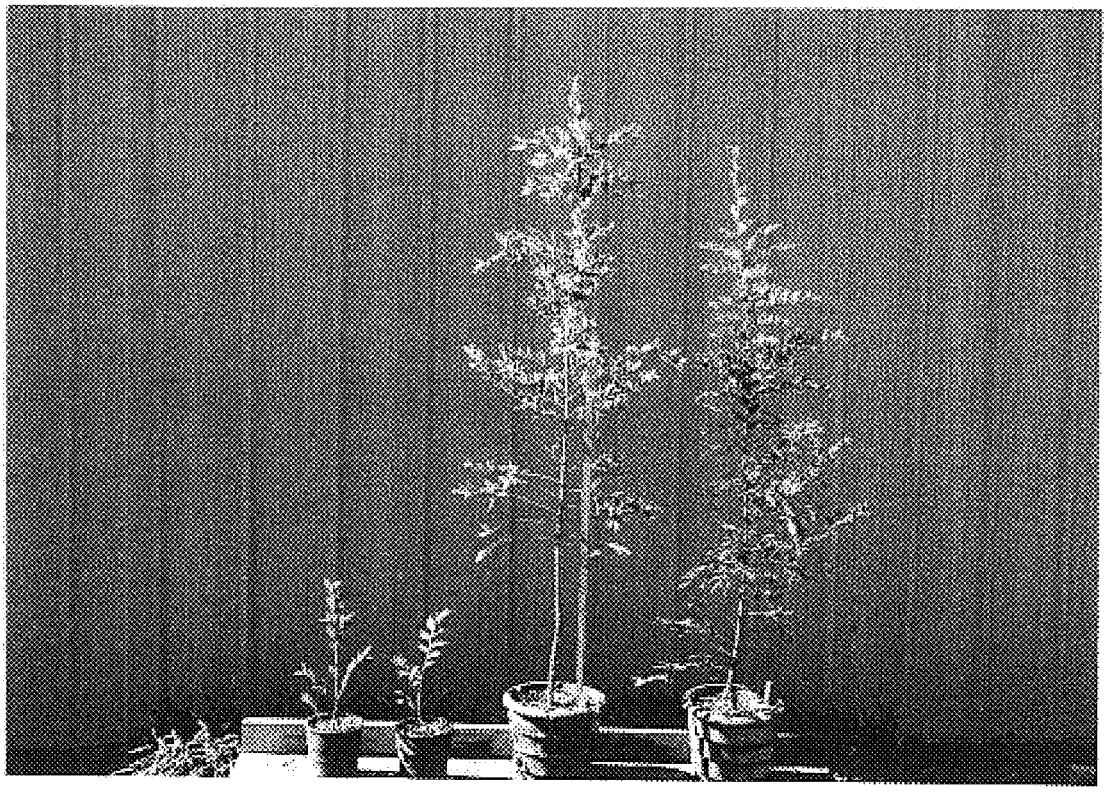
FIG. 8 is a full color photographic view of asexually reproduced offspring from my invention after three months and 15 months following rooting of cuttings.

Growth habit: Strongly upright central leader when young, as shown in FIG. 8, and becoming more oval with age, as shown in FIG. 1. The apical dominance of the central leader declines with age, leading to a broad oval form.

Origin: An open pollinated cross in an elm selection/breeding program in Stillwater, Okla.

Parentage: The parent plant of my new cultivar was a fourth generation seedling taken from an unknown tree in Sian, China in 1914. The parent plant originated from seeds taken from seedlings planted in 1997, which originated from seedlings planted in 1988, which originated from seeds collected from a mature lacebark elm in Woodward, Okal. in 1972, which originated from seeds collected from an unknown tree in Sian, China. The seeds were gathered selectively from each generation of trees having the better growth habit. The lacebark elm tree in Woodward, Okla. is still growing.

Propagation: The plant is easy to propagate from softwood cuttings collected during May, June and July in north central Oklahoma, with the distinguishing characteristics of the asexually propagated offspring remaining identical to the parent. Use of chlorinated water during the rooting process, rather than using, for example, untreated river water, lake water or pond water, helps prevent Phytophthora root rot in the plants.

Size and shape: The growth habit of my new cultivar is characterized as having an oval tree form with a strong central leader during the first four to six years following propagation. Once attaining a height of between about 10 and 14 feet, control by the central leader diminishes and branches form a broader oval crown. Branches are produced in abundance along the main stem when young and are typically between about 70 and 80 degrees from vertical. The branches are alternately spaced between about one and three inches apart. As the tree matures, the angles of the branches occurring in the lower five to eight feet up the central stem are between about 35 and 45 degrees. At a height of about 10 to 14 feet, the angle of the branches is between about 30 and 35 degrees. In north central Oklahoma, the plant size is characterized as having a height of between about 30 and about 50 feet.

Vigor: The cultivar of the present invention is vigorous, especially in the early spring through early summer, continuing into midsummer when moisture is adequate. Cuttings taken in early June or July root but grow little during the remainder of the summer. The following year, growth is typically between about 4 and about 6 feet when the plants are provided with good nursery conditions including, inter alia, nutrition and water management.

Hardiness: USDA hardiness zones 5 through 9.

General health and pest susceptibility: The foliage of the lacebark elm 'Whit XXX' has remained pest free in central Oklahoma. The stems of the plant have remained free from Nectria canker. The tree is also very resistant to *Cercospora* leaf spot disease.

FOLIAGE

Leaf persistence: Deciduous.

Arrangement on stems: Alternate.

Figure 2:
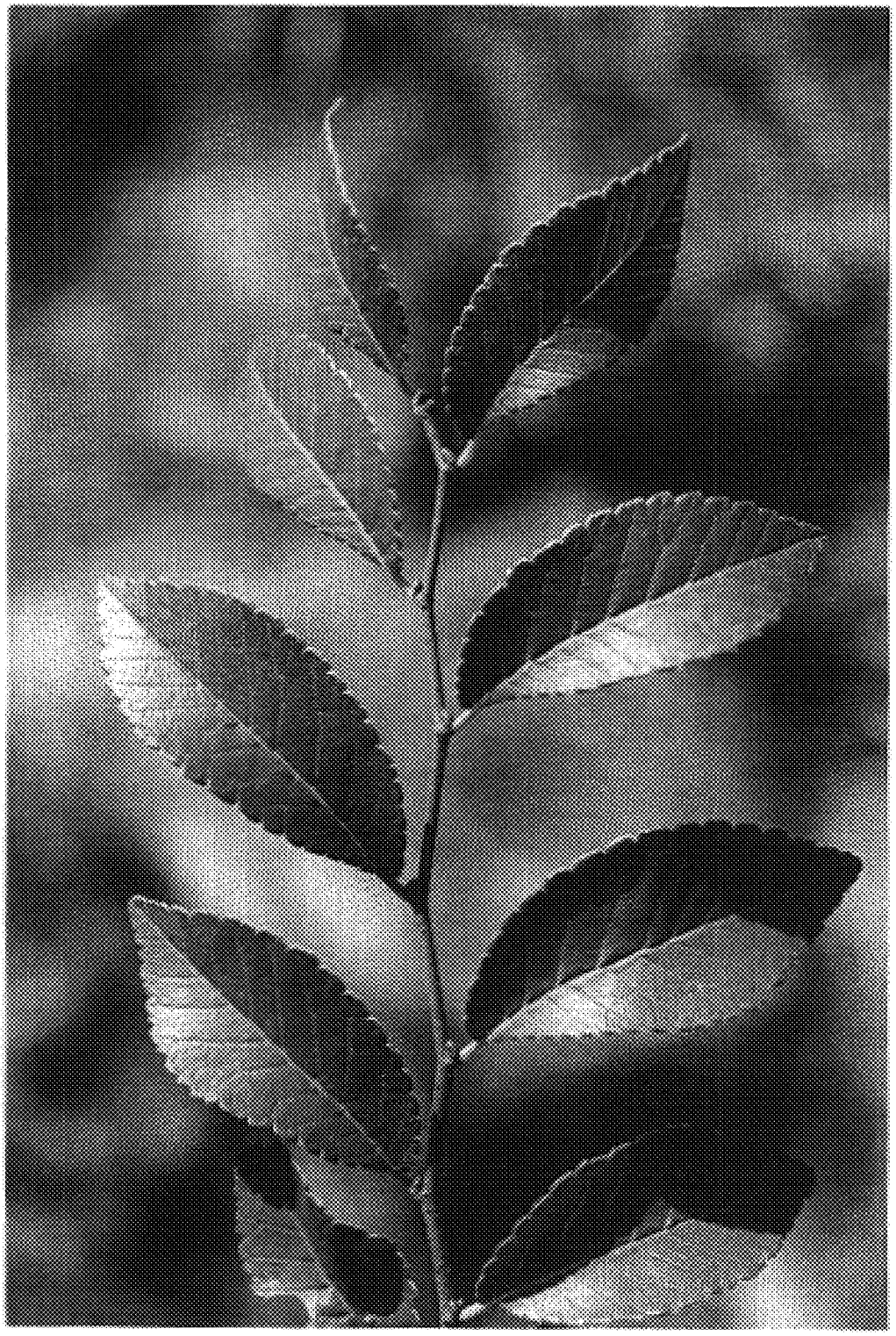
FIG. 2 is a full color photographic view of mature leaves on a twig produced during early to mid spring.
Figure 3:
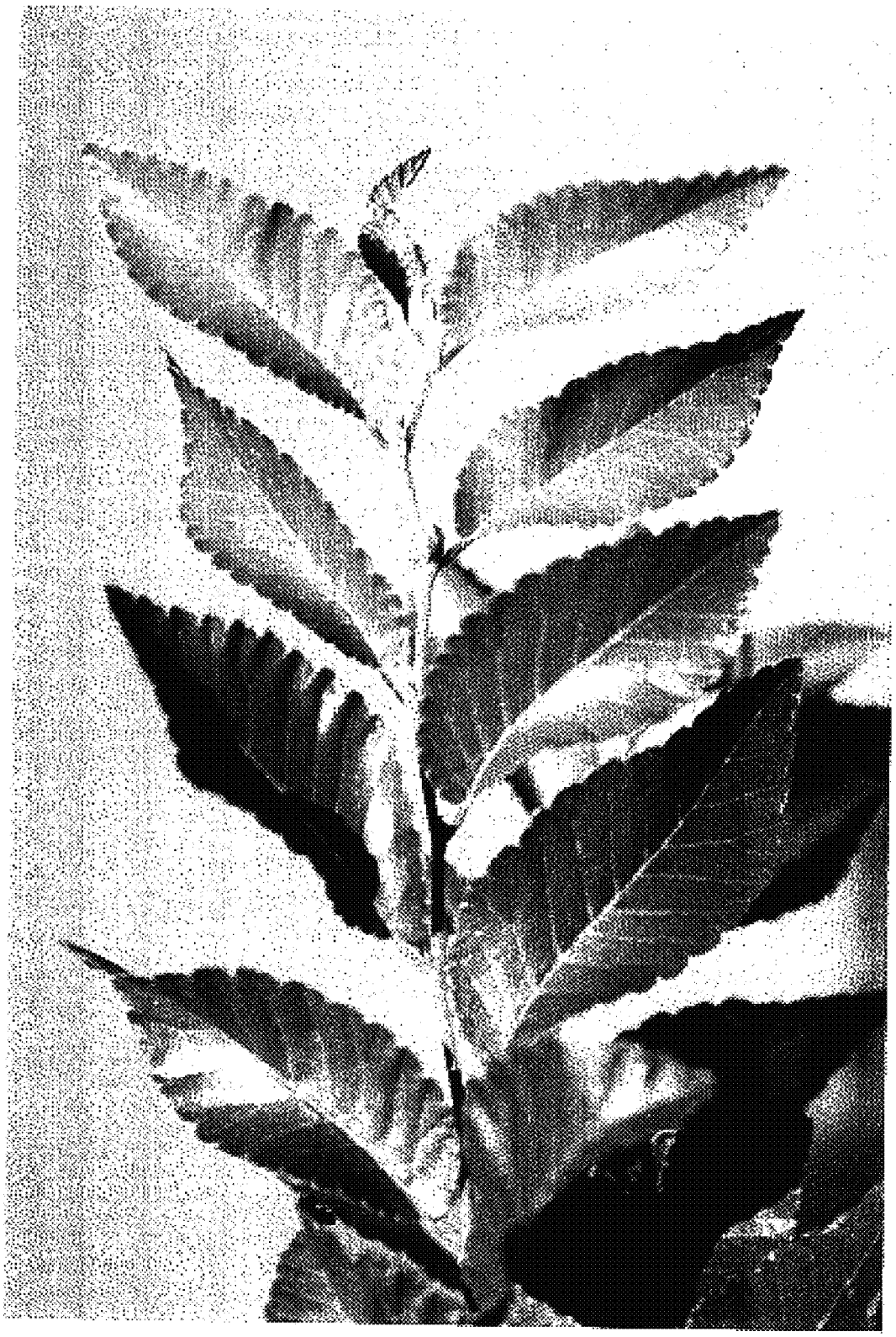
FIG. 3 is a full color photographic view of leaves ranging from very young to being fully expanded on a young twig produced during summer on the tree shown in FIG. 1.

Shape of leaves: As shown in FIGS. 2 and 3, the overall leaf shape is oblique, with acute leaf tips that are short and pointed. The leaf base is oblique with the two sides slightly unequal.

Size of leaves: Typically, the leaves are small, between about 0.75 and about 2 inches long and between about 0.5 and about 1 inch wide with spring growth. Vigorous summer shoots may produce leaves that are between about 1 and about 3 inches long and between about 0.75 and about 1.5 inches wide.

Margins of leaves: Serrate, occasionally doubly serrate.

Quantity: Singles that alternate on the twig.

Color of leaves: Young and intermediate aged leaves are shiny and light, yellow-green (144-A) on the upper surface and slightly lighter green (147-B or C) on the lower surface. The petioles are light green (147-C or D). Mature leaves are shiny and dark yellow-green (147-A) on the upper surface and slightly lighter (147-B) on the lower surface. The petioles are yellow-green (147-C).

Mature leaves in fall remain the same color and remain attached to the twigs. Only after several light frosts do upper portions of the leaves exposed to sun turn dull purple (183-A or B or C), while portions of leaves shaded by other leaves remain the mature color. Leaf drop typically does not occur until one or more hard freezes. Fall color is more pronounced during years when temperatures drop gradually and less when a early hard freeze causes leaves to drop.

Leaf venation: The upper leaf mid veins are a greyed-green (195-A or B) while the secondary veins on the upper surface are a dark green (137-A or B). On the underside of the leaf surface, the mid veins are brown (200-A) due to very fine hairs while the secondary veins are greyed-green (197-A or B).

Texture of leaves: The leaves are leathery, with a slightly scabrous upper surface. The lower surface is glabrous both with prominent veins.

Leaf petiole: Short and stout, typically between about ⅛ and about ¼ inch long. The petiole surface is covered with fine brown (200-A) hairs. Color descriptions are provided, supra.

Stipules: None.

Figure 5:
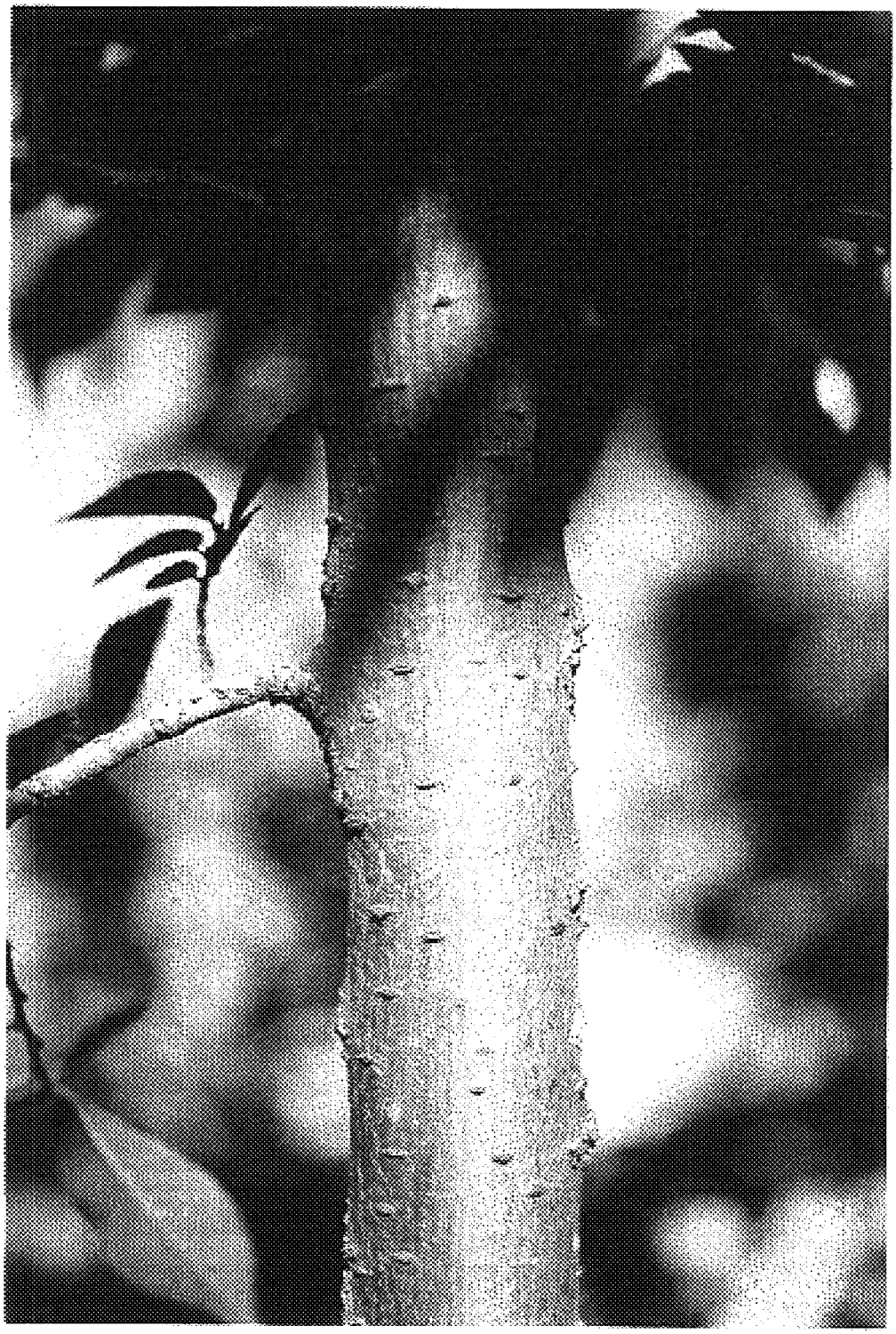
FIG. 5 is a full color photographic view of a section of stem about two inches diameter.
Figure 6:
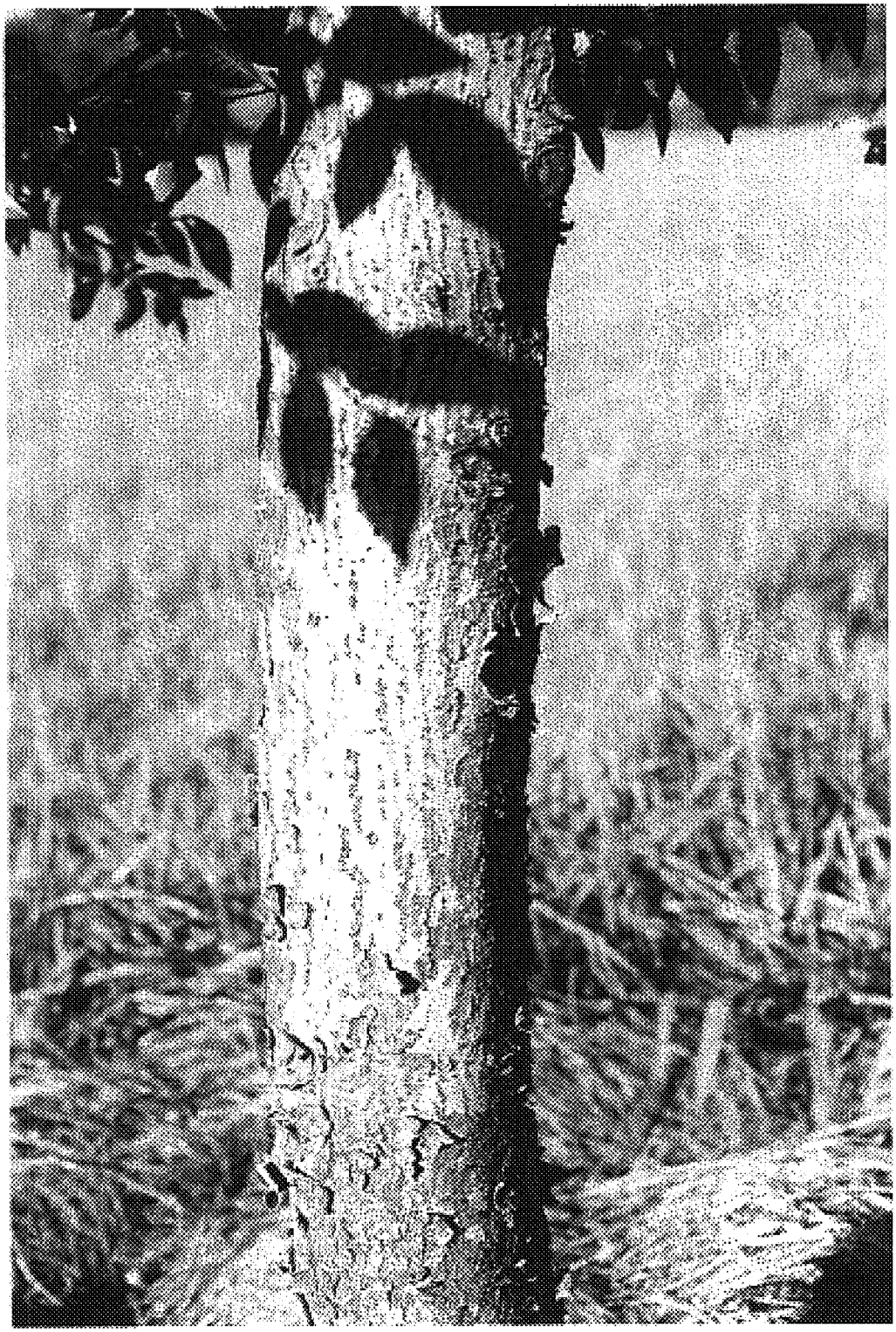
FIG. 6 is a full color photographic view of a section of stem about four inches diameter from the tree shown in FIG. 1.
Figure 7:
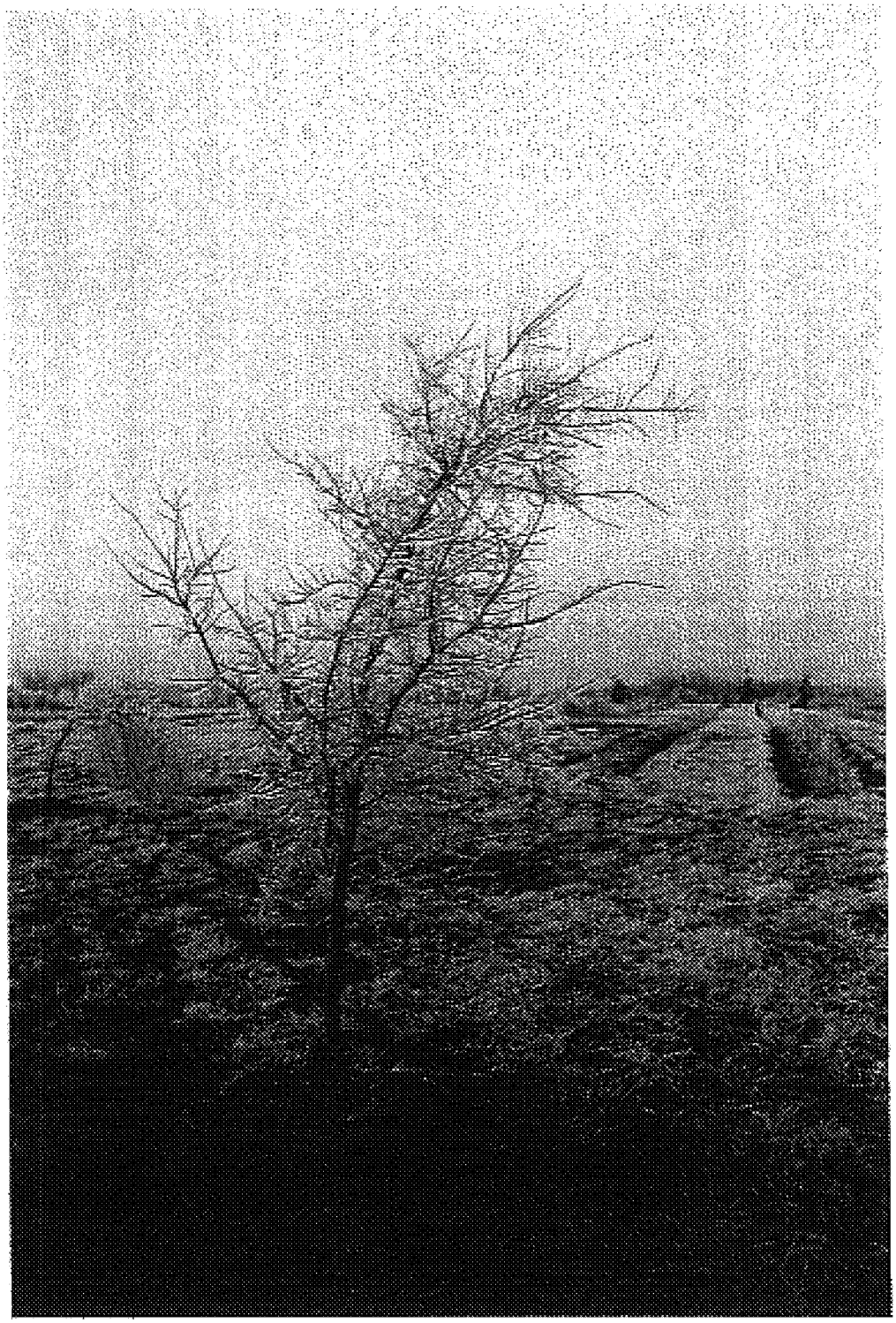
FIG. 7 is a full color photographic view comparing my new lacebark elm tree following a severe ice event with a severely ice-damaged tree of the same species, age and size.

Stems: The stem color changes with size. Young twigs are yellow-green (146-A or B or C) and scabrous. Stems having a diameter between about ¼ and about 1 inch are grey-green (197-A or B) while stems having a diameter of about 2 inches are grey (201-A or B or 197-A). Stems having a diameter of between about 3.5 inches and about 4 inches are mottled and have patches of different colors: patches of grey-green (197-A, B or C), patches of grey (201-A or B) and patches of brownish-orange (177-B, C or D). The lenticles are brownish-orange (177-A, B or C or 172-A or B). The stems are shown in detail in FIGS. 5 and 6, which clearly show the bark.

Stem and trunk lenticels: The lenticles are narrow elongate, having a width vertically of between about 1 and about 1.5 mm on all stems and branches. The length of lenticels around the stems about 1 inch diameter or less are typically about 1 mm but with an occasional lenticel having a length of between about 4 and 5 mm.

Dormant vegetative buds: The buds are elongated, sharp pointed and scabrous and are located in leaf axils. The dormant buds are typically between about 2 and about 3 mm long and between about 1 and about 1.5 mm wide with a more or less conical shape. They are brown in color (200-A).

FLOWERS and FRUITS

Figure 4:
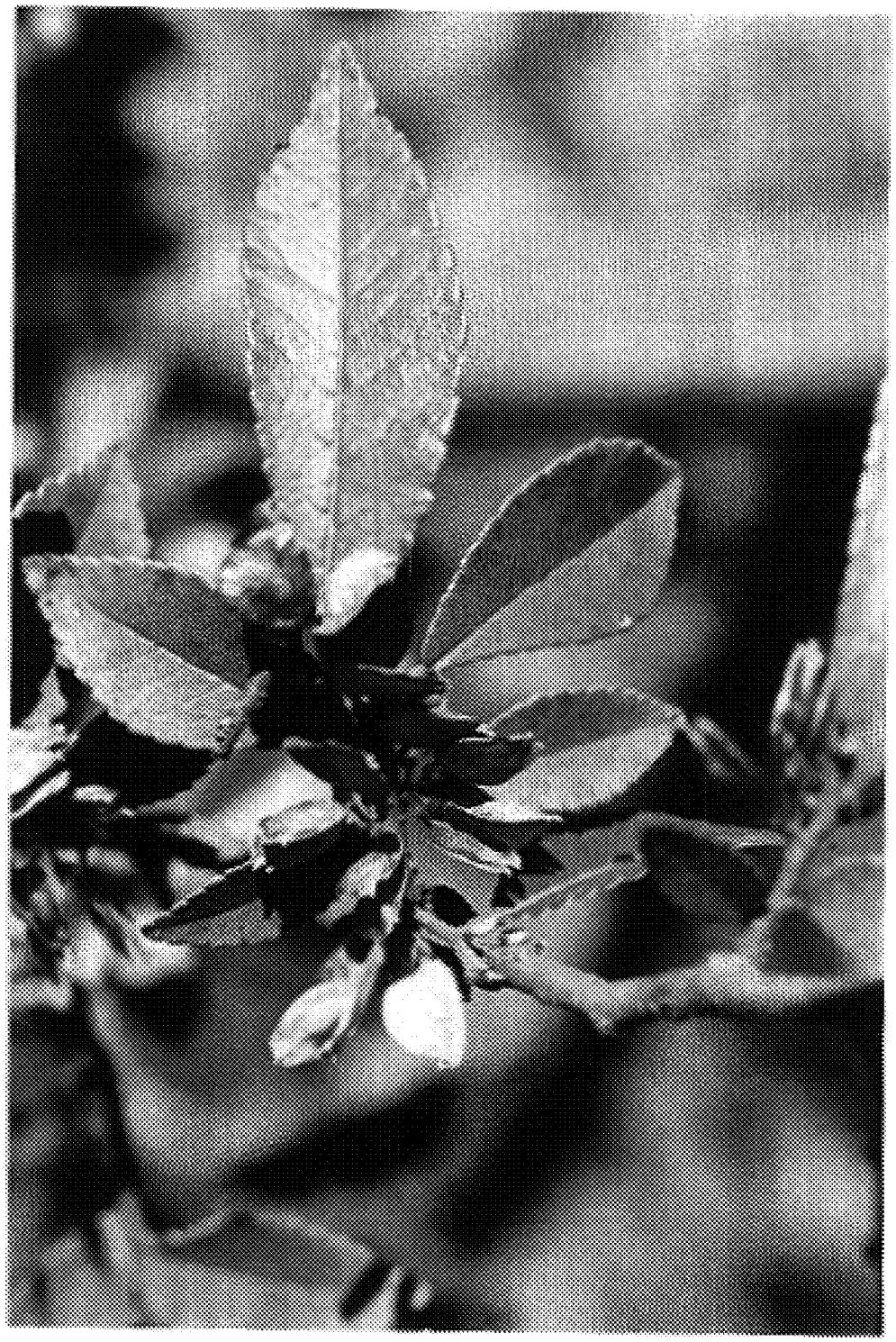
FIG. 4 is a full color photographic view of green young seeds, reddish purple seeds of intermediate development, and light tan mature seeds.

The flowers are typical of the species, characterized as being inconspicuous and occurring in early to mid-September in north central Oklahoma. The fruit is an elliptic-ovate samara between about ¼ and about ⅜ inch. Samara, as shown in FIG. 4, is at first light-green (139-C or D), then reddish-purple (67-A, B or C) and then light tan (199-B, C or D) at maturity. Fruit production is very light compared to other trees of the species and to date, no seeds have been viable.

I claim:

1. A new and distinct variety of lacebark elm tree, substantially as illustrated and described.

* * * * *